United States Patent [19]

Wakasugi et al.

[11] Patent Number: 5,426,240
[45] Date of Patent: Jun. 20, 1995

[54] PROCESS FOR THE CO-PRODUCTION OF DICHLOROACETALDEHYDE HYDRATE AND CHLORAL

[75] Inventors: Takashi Wakasugi; Tadashi Miyakawa; Fukuichi Suzuki, all of Fukushima, Japan

[73] Assignee: Kureha Chemical Industry Co., Ltd., Tokyo, Japan

[21] Appl. No.: 271,779

[22] Filed: Jul. 7, 1994

[30] Foreign Application Priority Data

Jul. 15, 1993 [JP] Japan .................. 5-196746

[51] Int. Cl.⁶ .................. C07C 45/63; C07C 45/00
[52] U.S. Cl. .................. 568/490; 568/491; 568/492
[58] Field of Search .................. 568/449, 490, 491, 495

[56] References Cited

U.S. PATENT DOCUMENTS

| | | | |
|---|---|---|---|
| 3,381,036 | 4/1968 | Clark et al. | 568/490 |
| 3,888,821 | 6/1975 | Milford, Jr. | 260/45.8 |
| 4,112,016 | 9/1978 | Moulds | 260/45.8 |
| 4,579,976 | 4/1986 | Chemical et al. | 568/490 |
| 5,248,832 | 9/1993 | Lee | 568/466 |

FOREIGN PATENT DOCUMENTS

| | | |
|---|---|---|
| 0457149 | 11/1991 | European Pat. Off. . |
| 2306335 | 9/1974 | Germany .................. 568/490 |
| 49-10032 | 1/1974 | Japan . |
| 45-75824 | 7/1974 | Japan . |
| 50-12322 | 2/1975 | Japan . |
| 50-14816 | 2/1975 | Japan . |
| 53-35020 | 4/1978 | Japan . |
| 3817158 | 7/1983 | Japan . |
| 62-26332 | 4/1987 | Japan . |
| 6414317 | 1/1989 | Japan . |
| 6485316 | 3/1989 | Japan . |
| 1204533 | 9/1989 | Japan . |
| 3143922 | 6/1991 | Japan . |
| 59293 | 1/1993 | Japan . |

OTHER PUBLICATIONS

Dokl Akod. Nank, BSSR, 23 (4), 347, (1979) Japan.
Appl. Polym. Sci 23(8), 2225–2231 (1979)"The Influence of Anilino–Substituted Salicylanilide on the Physicomechanical Properties of Ultraviolet Aged Natural Rubber" W. M. Khalifa.

Primary Examiner—Werren B. Lone
Attorney, Agent, or Firm—Burgess, Ryan & Wayne

[57] ABSTRACT

A process for producing dichloroacetaldehyde hydrate together with chloral from acetaldehyde or para-aldehyde. The process comprises a step of chlorinating acetaldehyde or para-aldehyde to obtain a chlorinated solution containing dichloroacetaldehyde as a major component, a step of distilling this chlorinated solution to obtain a distillate having a boiling point of 90°–100° C. and containing 50% or more of dichloroacetaldehyde, a step of adding water to this distillate, crystallizing dichloroacetaldehyde hydrate, and separating the crystals, and a step of chlorinating the remaining aldehyde components into chloral. The process enables dichloroacetaldehyde hydrate to be separated at a high purity and the raw materials to be utilized efficiently.

6 Claims, No Drawings

PROCESS FOR THE CO-PRODUCTION OF DICHLOROACETALDEHYDE HYDRATE AND CHLORAL

BACKGROUND OF THE INVENTION

1. Field of the Invention

The present invention relates to a process for producing dichloroacetaldehyde hydrate together with chloral from acetaldehyde or para-aldehyde.

2. Description of the Background Art

Dichloroacetaldehyde (hereinafter abbreviated as DCA) is a compound useful as a raw material for the synthesis of drugs and agricultural chemicals. Because this compound is extremely unstable, it has been supplied as an aqueous solution. In the past, hydrate of DCA was manufactured by the method of chlorinating 1,2-dichloroethylene using a method described, for example, in Deutsche Offenlegungsschrift 2306335. This method is not practiced at the present time, because 1,2-dichloroethylene is obtained only with difficulty.

Chloral, on the other hand, is manufactured by the chlorination of acetaldehyde or para-aldehyde. DCA is known to be produced in the course of this chlorination process. The process, however, cannot produce DCA alone; DCA is obtained together with monochloroacetaldehyde and chloral which have chlorination degrees different from that of DCA. Boiling points of these chlorinated acetaldehyde compounds are very close to each other. No method has been known to efficiently separate DCA from the mixture. Because of this reason, the production of DCA by the chlorination of acetaldehyde or para-aldehyde has not been practiced.

In view of this situation, the present inventors have undertaken extensive studies with an object of developing a process for producing DCA hydrate from raw materials which are available at low costs, and completed the present invention, by which DCA can be produced as a hydrate together with chloral from acetaldehyde or para-aldehyde.

As a result, the present inventors have found that high purity DCA hydrate crystals can be obtained if a mixture of chlorinated acetaldehydes with different chlorination degrees, which is obtained by the chlorination of acetaldehyde or para-aldehyde (hereinafter these are collectively called raw material aldehydes), is crystallized under specific conditions, and that the remaining raw material aldehydes can be effectively utilized by converting them into chloral hydrate. These findings have led to the completion of the present invention.

SUMMARY OF THE INVENTION

Accordingly, an object of the present invention is to provide a process for producing DCA hydrate together with chloral from acetaldehyde or para-aldehyde.

Another object of the present invention is to provide a process for separating crystals of DCA hydrate from the chlorinated solution obtained by the chlorination of acetaldehyde or para-aldehyde.

As a preferred embodiment, the present invention provides a process for producing DCA hydrate together with chloral from acetaldehyde or para-aldehyde, which comprises a step of chlorinating acetaldehyde or para-aldehyde to obtain a chlorinated solution containing DCA as a major component, a step of distilling this chlorinated solution to obtain a distillate having a boiling point of 90-100° C. and containing 50% or more of DCA, a step of adding water to this distillate, crystallizing DCA hydrate, and separating the crystals, and a step of chlorinating the remaining aldehyde components into chloral.

Other and further objects, features and advantages of the present invention will appear more fully from the following description.

DETAILED DESCRIPTION OF THE INVENTION AND PREFERRED EMBODIMENTS

In the present invention, acetaldehyde and para-aldehyde are first chlorinated to produce DCA. The chlorination is carried out by introducing first chlorine gas alone and then chlorine gas and water into raw material aldehydes until the chlorination degree, as defined to be an average number of chlorine atoms bonded to one mol of acetaldehyde, is about 1.9–2.3, preferably 2.2–2.3. A chlorinated solution containing 50% or more of DCA can be obtained in this manner. This chlorinated solution typically contains, besides DCA, about 30% of chloral, about 1% of monochloroacetaldehyde, and about 12% of water.

The chlorinated solution thus obtained is subjected to distillation, whereby unreacted chlorine gas is first distilled off and then a distillate having a boiling point of 90°–100° C. and containing 50% or more of DCA can be obtained. This distillate typically contains about 58% of DCA, about 30% of chloral, about 0.5% of monochloroacetaldehyde, and about 8% of water.

DCA hydrate is crystallized by adding water to this distillate. In this instance, an amount of water to make the solution 10–30% water is added. If the amount of water is less than 10%, the crystals grow slowly because the solution has high viscosity. If it is more than 30%, the crystal yield is low. Crystals of DCA hydrate deposit by thus adjusting the amount of water, controlling the temperature at 20° C. or lower, preferably at 5°–15° C., and further by adding crystal seeds as needed, while stirring the solution. If the temperature is higher than 20° C., the yield of DCA hydrate crystals is low; if it is lower than 5° C., the purity of the DCA hydrate obtained is low because of inclusion of chloral hydrate which may also crystallize at such a low temperature.

Deposited crystals of DCA hydrate are separated by centrifuge or filtration. The filtrate obtained by the separation of crystals is a solution containing DCA, chloral, and water. This filtrate is combined with distillation fractions, other than the above distillate containing 50% or more of DCA, and the distillation residue. The mixture is further chlorinated to produce chloral. In this manner, almost all aldehydes not obtained as DCA can be converted into chloral.

According to the process of the present invention, it is possible to manufacture DCA hydrate from readily available and inexpensive raw materials by chlorinating them in two steps, while introducing a step of separating DCA hydrate by crystallization between the chlorination steps. Because all other components derived from raw material aldehydes can be converted into chloral which is a useful industrial chemical, loss of raw material is extremely low and the process is thus very economical. Also, there are almost no problems of waste disposal.

About 10% of chlorination raw materials, acetaldehyde or para-aldehyde, can be converted to DCA hydrate by the process of the present invention, with the remaining raw materials being recovered as chloral. Thus, almost all raw materials can be effectively utilized without loss.

Other features of the invention will become apparent in the course of the following description of the exemplary embodiments which are given for illustration of the invention and are not intended to be limiting thereof.

EXAMPLES

Example 1
Preparation of chlorination liquid

Into a 3 l three-necked flask equipped with a stirrer, a condenser, and a thermometer were charged 500 g of para-aldehyde and 5 ml of water. Chlorine gas was introduced into this solution maintained at 10° C. at a rate of 150 ml/min to initiate the chlorination reaction. Then, chlorine gas was introduced at a rate of 150 to 900 ml/min for 14 hours, initially maintaining the temperature at 2±1° C. In the chlorination step, 200 g of water was added slowly after the chlorination degree reached 1.0, while raising the temperature to as high as 40° C. at the point of chlorination degree of 2.3. Hydrogen chloride gas produced by the chlorination reaction as a by-product was absorbed in an aqueous solution of sodium hydroxide.

Distillation

The chlorinated solution (about 1500 g) was distilled at 90° to 100° C. under atmospheric pressure to obtain 900 g of a distillate. This distillate was confirmed to contain 1% of monochloroacetaldehyde, 54% of DCA hydrate, 33% of chloral, and 10% of water and other high boiling point components by gas chromatographic analysis and water-content measurement.

Crystallization

The crystallization of DCA hydrate was carried out using a 3 l three-necked flask equipped with a stirrer and a thermometer. 100 g of water was added to 900 g of the distillate having the above composition and the mixture was kept at 15° C. After the addition of a small amount of DCA hydrate crystals as crystal seeds, this mixture was gradually cooled at a rate of 1° C. per hour to as low as 7°–8° C., at which temperature the mixture was maintained for 15 hours while stirring to complete the crystallization.

Separation of crystals

Crystals thus obtained were separated by filtration to obtain 195 g of white crystals of DCA hydrate with a purity of 98.5%. The crystals were washed with 10 g of water, thus obtaining 180 g of DCA hydrate having a purity of 99.5%.

Production of chloral

The distillation residue and distillates distilled at less than 90° C., obtained in the distillation of the chlorinated liquid, were combined with the filtrate and the washings in the separation step of DCA hydrate. The mixture was chlorinated to convert the aldehydes components into chloral.

As a result, about 12% of the raw material para-aldehyde was converted into DCA hydrate and about 83% to chloral, with the utilization of the para-aldehyde being 95%.

Obviously, numerous modifications and variations of the present invention are possible in light of the above teachings. It is therefore to be understood that within the scope of the appended claims, the invention may be practiced otherwise than as specifically described herein.

What is claimed is:

1. A process for producing dichloroacetaldehyde hydrate together with chloral from acetaldehyde or para-aldehyde, which comprises, chlorinating acetaldehyde or para-aldehyde to obtain a chlorinated solution containing dichloroacetaldehyde as a major component, distilling this chlorinated solution to obtain a distillate having a boiling point of 90°–100° C. and containing 50% or more of dichloroacetaldehyde, adding water to this distillate, crystallizing dichloroacetaldehyde hydrate, and separating the crystals, and chlorinating the remaining aldehyde components into chloral.

2. The process according to claim 1, wherein the distillation is carried on the chlorinated solution of acetaldehyde and para-aldehyde with a chlorination degree of 1.9–2.3.

3. The process according to claim 1, wherein the solution subjected to the crystallization of dichloroacetaldehyde hydrate contains 10–30% of water.

4. The process according to claim 1, wherein dichloroacetaldehyde hydrate crystals are added as seed crystals.

5. The process according to claim 1, wherein the crystallization temperature is 5°–15° C.

6. A process for producing dichloroacetaldehyde hydrate which comprises, adding 10–30% of water to a chlorinated solution of acetaldehyde or para-aldehyde which contains 50% or more of dichloroacetaldehyde, crystallizing dichloroacetaldehyde hydrate while maintaining the solution at a temperature below 20° C., and separating the crystals.

* * * * *